United States Patent
Matsui et al.

(10) Patent No.: US 9,040,280 B2
(45) Date of Patent: May 26, 2015

(54) PROTEASE VARIANTS

(75) Inventors: Tomoko Matsui, Chiba (JP); Allan Noergaard, Chiba (JP); Thomas Agersten Poulsen, Ballerup (DK); John Matthews, Louisburg, NC (US)

(73) Assignee: NOVOZYMES A/S, Bagsvaerd (DK)

( * ) Notice: Subject to any disclaimer, the term of this patent is extended or adjusted under 35 U.S.C. 154(b) by 274 days.

(21) Appl. No.: 13/510,076

(22) PCT Filed: Dec. 10, 2010

(86) PCT No.: PCT/US2010/059814
§ 371 (c)(1),
(2), (4) Date: May 16, 2012

(87) PCT Pub. No.: WO2011/072191
PCT Pub. Date: Jun. 16, 2011

(65) Prior Publication Data
US 2012/0309067 A1     Dec. 6, 2012

Related U.S. Application Data

(60) Provisional application No. 61/285,601, filed on Dec. 11, 2009.

(51) Int. Cl.
*C12N 9/48*     (2006.01)
*C12N 9/58*     (2006.01)

(52) U.S. Cl.
CPC .. *C12N 9/58* (2013.01); *Y02E 50/17* (2013.01)

(58) Field of Classification Search
CPC ................................ C12N 9/50; C12N 9/58
See application file for complete search history.

(56) References Cited

FOREIGN PATENT DOCUMENTS

WO        03/048353 A1     6/2003

OTHER PUBLICATIONS

Merheb-Dini et al, J Agric Food Chem, vol. 57, pp. 9210-9217 (2009).

*Primary Examiner* — Sheridan Swope
(74) *Attorney, Agent, or Firm* — Michael W. Krenicky

(57) ABSTRACT

The present invention relates to proteases having at least 75% identity to a protease derived from *Thermoascus aurantiacus* and comprises at least one modification in the amino acid sequence thereof. These protease variants have improved thermostability. The invention also relates to DNA encoding these proteases, methods of their production, as well as the use thereof.

4 Claims, No Drawings

SEQUENCE LISTING

<160> NUMBER OF SEQ ID NOS: 6

<210> SEQ ID NO 1
<211> LENGTH: 1068
<212> TYPE: DNA
<213> ORGANISM: Thermoascus aurantiacus
<220> FEATURE:
<221> NAME/KEY: sig_peptide
<222> LOCATION: (1)..(57)
<220> FEATURE:
<221> NAME/KEY: CDS
<222> LOCATION: (1)..(1065)
<220> FEATURE:
<221> NAME/KEY: misc_feature
<222> LOCATION: (58)..(534)
<220> FEATURE:
<221> NAME/KEY: mat_peptide
<222> LOCATION: (535)..(1068)

<400> SEQUENCE: 1

```
atg cgg ctc gtt gct tcc cta acg gcc ttg gtg gcc ttg tcc gta         45
Met Arg Leu Val Ala Ser Leu Thr Ala Leu Val Ala Leu Ser Val
        -175             -170             -165 cct gtc ttt ccc gct gct gtc aac gtg aag cgt gct tcg tcc tac         90
Pro Val Phe Pro Ala Ala Val Asn Val Lys Arg Ala Ser Ser Tyr
        -160             -155             -150 ctg gag atc act ctg agc cag gtc agc aac act ctg atc aag gcc        135
Leu Glu Ile Thr Leu Ser Gln Val Ser Asn Thr Leu Ile Lys Ala
        -145             -140             -135 gtg gtc cag aac act ggt agc gac gag ttg tcc ttc gtt cac ctg        180
Val Val Gln Asn Thr Gly Ser Asp Glu Leu Ser Phe Val His Leu
        -130             -125             -120 aac ttc ttc aag gac ccc gct cct gtc aaa aag gta tcg gtc tat        225
Asn Phe Phe Lys Asp Pro Ala Pro Val Lys Lys Val Ser Val Tyr
        -115             -110             -105 cgc gat ggg tct gaa gtg cag ttc gag ggc att ttg agc cgc tac aaa    273
Arg Asp Gly Ser Glu Val Gln Phe Glu Gly Ile Leu Ser Arg Tyr Lys
        -100             -95              -90 tcg act ggc ctc tct cgt gac gcc ttt act tat ctg gct ccc gga gag   321
Ser Thr Gly Leu Ser Arg Asp Ala Phe Thr Tyr Leu Ala Pro Gly Glu
        -85              -80              -75 tcc gtc gag gac gtt ttt gat att gct tcg act tac gat ctg acc agc   369
Ser Val Glu Asp Val Phe Asp Ile Ala Ser Thr Tyr Asp Leu Thr Ser
        -70              -65              -60 ggc ggc cct gta act atc cgt act gag gga gtt gtt ccc tac gcc acg   417
Gly Gly Pro Val Thr Ile Arg Thr Glu Gly Val Val Pro Tyr Ala Thr
-55                      -50                              -40
                                 -45 gct aac agc act gat att gcc ggc tac atc tca tac tcg tct aat gtg   465
Ala Asn Ser Thr Asp Ile Ala Gly Tyr Ile Ser Tyr Ser Ser Asn Val
                -35              -30              -25
```

```
ttg acc att gat gtc gat ggc gcc gct gct gcc act gtc tcc aag gca    513
Leu Thr Ile Asp Val Asp Gly Ala Ala Ala Ala Thr Val Ser Lys Ala
        -20             -15                 -10 atc act cct ttg gac cgc cgc act agg atc agt tcc tgc tcc ggc agc    561
Ile Thr Pro Leu Asp Arg Arg Thr Arg Ile Ser Ser Cys Ser Gly Ser
     -5               -1   1               5 aga cag agc gct ctt act acg gct ctc aga aac gct gct tct ctt gcc    609
Arg Gln Ser Ala Leu Thr Thr Ala Leu Arg Asn Ala Ala Ser Leu Ala
 10              15                  20                  25 aac gca gct gcc gac gcg gct cag tct gga tca gct tca aag ttc agc    657
Asn Ala Ala Ala Asp Ala Ala Gln Ser Gly Ser Ala Ser Lys Phe Ser
                 30                  35                  40 gag tac ttc aag act act tct agc tct acc cgc cag acc gtg gct gcg    705
Glu Tyr Phe Lys Thr Thr Ser Ser Ser Thr Arg Gln Thr Val Ala Ala
             45                  50                  55 cgt ctt cgg gct gtt gcg cgg gag gca tct tcg tct tcg gga gcc        753
Arg Leu Arg Ala Val Ala Arg Glu Ala Ser Ser Ser Ser Gly Ala
         60                  65                  70 acc acg tac tac tgc gac gat ccc tac ggc tac tgt tcc tcc aac gtc    801
Thr Thr Tyr Tyr Cys Asp Asp Pro Tyr Gly Tyr Cys Ser Ser Asn Val
 75                  80                  85 ctg gct tac acc ctg cct tca tac aac ata atc gcc aac tgt gac att    849
Leu Ala Tyr Thr Leu Pro Ser Tyr Asn Ile Ile Ala Asn Cys Asp Ile
 90                  95                 100                 105 ttc tat act tac ctg ccg gct ctg acc agt acc tgt cac gct cag gat    897
Phe Tyr Thr Tyr Leu Pro Ala Leu Thr Ser Thr Cys His Ala Gln Asp
             110                 115                 120 caa gcg acc act gcc ctt cac gag ttc acc cat gcg cct ggc gtc tac    945
Gln Ala Thr Thr Ala Leu His Glu Phe Thr His Ala Pro Gly Val Tyr
         125                 130                 135 agc cct ggc acg gac gac ctg gcg tat ggc tac cag gct gcg atg ggt    993
Ser Pro Gly Thr Asp Asp Leu Ala Tyr Gly Tyr Gln Ala Ala Met Gly
     140                 145                 150 ctc agc agc agc cag gct gtc atg aac gct gac acc tac gct ctc tat   1041
Leu Ser Ser Ser Gln Ala Val Met Asn Ala Asp Thr Tyr Ala Leu Tyr
 155                 160                 165 gcg aat gcc ata tac ctt ggt tgc taa                                1068
Ala Asn Ala Ile Tyr Leu Gly Cys
170                 175

<210> SEQ ID NO 2
<211> LENGTH: 355
<212> TYPE: PRT
<213> ORGANISM: Thermoascus aurantiacus

<400> SEQUENCE: 2

Met Arg Leu Val  Ala Ser Leu Thr Ala  Leu Val Ala Leu Ser  Val
         -175                 -170                 -165

Pro Val Phe Pro  Ala Ala Val Asn Val  Lys Arg Ala Ser Ser  Tyr
         -160                 -155                 -150

Leu Glu Ile Thr  Leu Ser Gln Val Ser  Asn Thr Leu Ile Lys  Ala
         -145                 -140                 -135

Val Val Gln Asn  Thr Gly Ser Asp Glu  Leu Ser Phe Val His  Leu
         -130                 -125                 -120

Asn Phe Phe Lys  Asp Pro Ala Pro Val  Lys Lys Val Ser Val  Tyr
         -115                 -110                 -105

Arg Asp Gly Ser  Glu Val Gln Phe Glu  Gly Ile Leu Ser Arg Tyr Lys
         -100                  -95                  -90
```

```
Ser Thr Gly Leu Ser Arg Asp Ala Phe Thr Tyr Leu Ala Pro Gly Glu
        -85             -80             -75

Ser Val Glu Asp Val Phe Asp Ile Ala Ser Thr Tyr Asp Leu Thr Ser
    -70             -65             -60

Gly Gly Pro Val Thr Ile Arg Thr Glu Gly Val Val Pro Tyr Ala Thr
-55             -50             -45             -40

Ala Asn Ser Thr Asp Ile Ala Gly Tyr Ile Ser Tyr Ser Asn Val
            -35             -30             -25

Leu Thr Ile Asp Val Asp Gly Ala Ala Ala Thr Val Ser Lys Ala
        -20             -15             -10

Ile Thr Pro Leu Asp Arg Arg Thr Arg Ile Ser Ser Cys Ser Gly Ser
        -5          -1  1               5

Arg Gln Ser Ala Leu Thr Thr Ala Leu Arg Asn Ala Ala Ser Leu Ala
10              15              20              25

Asn Ala Ala Ala Asp Ala Ala Gln Ser Gly Ser Ala Ser Lys Phe Ser
                30              35              40

Glu Tyr Phe Lys Thr Thr Ser Ser Thr Arg Gln Thr Val Ala Ala
            45              50              55

Arg Leu Arg Ala Val Ala Arg Glu Ala Ser Ser Ser Ser Gly Ala
        60              65              70

Thr Thr Tyr Tyr Cys Asp Asp Pro Tyr Gly Tyr Cys Ser Ser Asn Val
    75              80              85

Leu Ala Tyr Thr Leu Pro Ser Tyr Asn Ile Ile Ala Asn Cys Asp Ile
90              95              100             105

Phe Tyr Thr Tyr Leu Pro Ala Leu Thr Ser Thr Cys His Ala Gln Asp
            110             115             120

Gln Ala Thr Thr Ala Leu His Glu Phe Thr His Ala Pro Gly Val Tyr
            125             130             135

Ser Pro Gly Thr Asp Asp Leu Ala Tyr Gly Tyr Gln Ala Ala Met Gly
            140             145             150

Leu Ser Ser Ser Gln Ala Val Met Asn Ala Asp Thr Tyr Ala Leu Tyr
            155             160             165

Ala Asn Ala Ile Tyr Leu Gly Cys
170             175

<210> SEQ ID NO 3
<211> LENGTH: 49
<212> TYPE: DNA
<213> ORGANISM: Artificial sequence
<220> FEATURE:
<223> OTHER INFORMATION: Artificial primer

<400> SEQUENCE: 3
aacgacggta cccgggatc ggatccatgc ggctcgttgc ttccctaac        49

<210> SEQ ID NO 4
<211> LENGTH: 48
<212> TYPE: DNA
<213> ORGANISM: Artificial sequence
<220> FEATURE:
<223> OTHER INFORMATION: Artificial primer

<400> SEQUENCE: 4
ctaattacat gatgcggccc ttaattaatt agcaaccaag gtatatgg         48
```

```
<210> SEQ ID NO 5
<211> LENGTH: 20
<212> TYPE: DNA
<213> ORGANISM: Artificial sequence
<220> FEATURE:
<223> OTHER INFORMATION: Artificial primer

<400> SEQUENCE: 5
taggagttta gtgaacttgc                                           20

<210> SEQ ID NO 6
<211> LENGTH: 18
<212> TYPE: DNA
<213> ORGANISM: Artificial sequence
<220> FEATURE:
<223> OTHER INFORMATION: Artificial primer

<400> SEQUENCE: 6
ttcgagcgtc ccaaaacc                                             18
```

PROTEASE VARIANTS

CROSS-REFERENCE TO RELATED APPLICATIONS

This application is a 35 U.S.C. 371 national application of PCT/US2010/059814 filed Dec. 10, 2010 which claims priority or the benefit under 35 U.S.C. 119 of U.S. provisional application No. 61/285,601 filed Dec. 11, 2009 the contents of which are fully incorporated herein by reference.

REFERENCE TO SEQUENCE LISTING

This application contains a Sequence Listing in computer readable form. The computer readable form is incorporated herein by reference.

FIELD OF THE INVENTION

The present invention relates to a protease which has at least 75% identity to a protease derived from *Thermoascus aurantiacus*, the amino acid sequence of which is shown in the appended sequence listing as amino acids 1 to 177 of SEQ ID NO: 2, and comprises at least one modification as compared to this protease (i.e., is a variant thereof). The invention also relates to DNA encoding these proteases, nucleic acid constructs, vectors, and host cells comprising the polynucleotides as well as methods of their production, as well as the use thereof, e.g. in production of fermentation products, e.g., ethanol.

BACKGROUND OF THE INVENTION

Proteases are well-known enzymes, as are the advantages of applying them in production of fermentation products. Proteases have been isolated from various sources, including a number of fungal and bacterial strains.

It is an object of the present invention to provide alternative polypeptides having protease activity (protease variants) and polynucleotides encoding the polypeptides. It is also an object of the invention to provide protease of improved properties as compared to the parent protease from which they were derived. The protease variants of the invention exhibit improved thermostability compared to the wild type parent protease.

WO 2003/048353 discloses the wildtype protease of *Thermoascus aurantiacus* CGMCC No. 0670.

SUMMARY OF THE INVENTION

In a first aspect, the present invention relates to a method of producing a protease variant having protease activity and an improved thermostablity when compared to the wild-type parent protease, said method comprising culturing a cell into which has been introduced an expression vector comprising the following operably linked elements:
(a) a transcription promoter,
(b) a polynucleotide molecule encoding a protease variant which has at least 75% identity to the protease shown in amino acids 1 to 177 of SEQ ID NO: 2 and which comprises at least one modification as compared to amino acids 1 to 177 of SEQ ID NO: 2 in at least one position selected from the following: 27, 79, 82, 87, 112, 142, 2, 5, 6, 8, 26, 41, 43, 46, 49, 53, 54, 73, 88, 104, 114, 115, 116, 126, 152, 157, 158, and 173, which polynucleotide molecule is prepared by introducing at least one mutation into a DNA molecule encoding a protease, and
(c) a transcription terminator,
whereby said cell expresses the protease variant encoded by the polynucleotide molecule; and recovering the protease variant.

In a second aspect, the present invention relates to a protease which has at least 75% identity to amino acids 1 to 177 of SEQ ID NO: 2 and which comprises at least one modification as compared to amino acids 1 to 177 of SEQ ID NO: 2 in at least one position selected from the following: 27, 79, 82, 87, 112, 142, 2, 5, 6, 8, 26, 41, 43, 46, 49, 53, 54, 73, 88, 104, 114, 115, 116, 126, 152, 157, 158, and 173.

The invention also relates to a nucleic acid sequence encoding these proteases, a nucleic acid construct comprising the nucleic acid sequence, an expression vectors comprising the nucleic acid construct, a host cell comprising the expression vector and/or the nucleic acid construct.

The invention also relates to the use of the proteases, e.g. in a starch liquefaction, saccharirfication and/or fermentation process.

DETAILED DESCRIPTION OF THE INVENTION

The present invention relates to isolated variants of a parent protease, comprising a modification in at least one position corresponding to positions 27, 79, 82, 87, 112, 142, 2, 5, 6, 8, 26, 41, 43, 46, 49, 53, 54, 73, 88, 104, 114, 115, 116, 126, 152, 157, 158, and 173 of the mature polypeptide of SEQ ID NO: 2, wherein the variant has protease activity. In particular the variants according to the invention have improved thermosatbility.

Protease activity: The term "protease activity" means a polypeptide of EC. 3.4.-.-. In a preferred embodiment it is a polypeptide belonging to the EC 3.4.24 metalloendopeptidases. Protease activity may be determined according to the procedure described in Example 1, e.g. using azo-casein assay or endo-protease assay using protazyme OL.

The ENZYME site at the internet (i.e, www.expasy.ch/enzyme/) is a repository of information relative to the nomenclature of enzymes. It is primarily based on the recommendations of the Nomenclature Committee of the International Union of Biochemistry and Molecular Biology (IUB-MB) and it describes each type of characterized enzyme for which an EC (Enzyme Commission) number has been provided (Bairoch A. The ENZYME database, 2000, Nucleic Acids Res 28:304-305). See also the handbook Enzyme Nomenclature from NC-IUBMB, 1992).

Variant: The term "variant" means a polypeptide having protease activity comprising at least one modification, i.e., a substitution, insertion, and/or deletion, compared to the amino acid sequence shown as 1 to 177 of SEQ ID NO: 2. In the present context, "at least one" (e.g. modification) means one or more, e.g. 1, 2, 3, 4, 5, 6, 7, 8, 9, or 10 modifications; or 12, 14, 15, 16, 18, 20, 22, 24, 25, 28, or 30 modifications; and so on, up to a maximum number of modifications of 44. The protease variants of the invention, however, still have to be at least 75% identical to amino acids 1 to 177 of SEQ ID NO: 2. In another embodiment, the variant has at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% identity to amino acids 1 to 177 of SEQ ID NO: 2. In still further particular embodiments, the degree of identity is at least 98.0%, 98.2%, 98.4%, 98.6%, 98.8%, 99.0%, 99.1%, 99.2%, 99.3%, or at least 99.4%, but less than 100%, sequence identity with the mature polypeptide of SEQ ID NO: 2.

Mutant: The term "mutant" means a polynucleotide encoding a variant.

Wild-Type Enzyme: The term "wild-type" protease means a protease expressed by a naturally occurring microorganism, such as a bacterium, yeast, or filamentous fungus found in nature.

Parent or Parent Protease: The term "parent" or "parent protease" means a protease to which an alteration is made to produce the enzyme variants of the present invention. The parent may be a naturally occurring (wild-type) polypeptide or a variant thereof.

Parental variant: The term parental variant means that the starting point for making a variant protease was itself a variant compared to the wild type protease.

Isolated variant: The term "isolated variant" means a variant that is modified by the hand of man. In one aspect, the variant is at least 1% pure, e.g., at least 5% pure, at least 10% pure, at least 20% pure, at least 40% pure, at least 60% pure, at least 80% pure, and at least 90% pure, as determined by SDS-PAGE.

Substantially pure variant: The term "substantially pure variant" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the variant is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The variants of the present invention are preferably in a substantially pure form. This can be accomplished, for example, by preparing the variant by well known recombinant methods or by classical purification methods.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 177 of SEQ ID NO: 2. The signal peptide part can be predicted by programs known in the art (SignalP (Nielsen et al., 1997, *Protein Engineering* 10:1-6)). Amino acids 1 to 177 of SEQ ID NO: 2 is the expected mature part. Generally, the first amino acid of the mature part of an enzyme can be determined by N-terminal sequencing of the purified enzyme. The N-terminal of the mature polypeptide was confirmed by N-terminal sequencing. Any difference between the signal peptide part and the mature part must then be due to the presence of a propeptide.

Mature polypeptide coding sequence: The term "mature polypeptide coding sequence" means a polynucleotide that encodes a mature polypeptide having protease activity. In one aspect, the mature polypeptide coding sequence is nucleotides 535 to 1065 of SEQ ID NO: 1 based on SignalP (Nielsen et al., 1997, *Protein Engineering* 10:1-6) that predicts nucleotides 535 to 1065 of SEQ ID NO: 1 encode a signal peptide.

Sequence Identity: The relatedness between two amino acid sequences or between two nucleotide sequences is described by the parameter "sequence identity". For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Isolated polynucleotide: The term "isolated polynucleotide" means a polynucleotide that is modified by the hand of man. In one aspect, the isolated polynucleotide is at least 1% pure, e.g., at least 5% pure, at least 10% pure, at least 20% pure, at least 40% pure, at least 60% pure, at least 80% pure, at least 90% pure, and at least 95% pure, as determined by agarose electrophoresis. The polynucleotides may be of genomic, cDNA, RNA, semisynthetic, synthetic origin, or any combinations thereof.

Substantially pure polynucleotide: The term "substantially pure polynucleotide" means a polynucleotide preparation free of other extraneous or unwanted nucleotides and in a form suitable for use within genetically engineered polypeptide production systems. Thus, a substantially pure polynucleotide contains at most 10%, at most 8%, at most 6%, at most 5%, at most 4%, at most 3%, at most 2%, at most 1%, and at most 0.5% by weight of other polynucleotide material with which it is natively or recombinantly associated. A substantially pure polynucleotide may, however, include naturally occurring 5'- and 3'-untranslated regions, such as promoters and terminators. It is preferred that the substantially pure polynucleotide is at least 90% pure, e.g., at least 92% pure, at least 94% pure, at least 95% pure, at least 96% pure, at least 97% pure, at least 98% pure, at least 99% pure, and at least 99.5% pure by weight. The polynucleotides of the present invention are preferably in a substantially pure form.

Coding sequence: The term "coding sequence" means a polynucleotide, which directly specifies the amino acid sequence of its polypeptide product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" means all components necessary for the expression of a polynucleotide encoding a variant of the present invention. Each control sequence may be native or foreign to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Operably linked: The term "operably linked" means a configuration in which a control sequence is placed at an appropriate position relative to the coding sequence of a polynucleotide such that the control sequence directs the expression of the coding sequence.

Expression: The term "expression" includes any step involved in the production of the variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to additional nucleotides that provide for its expression.

Host cell: The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such improved properties include, but are not limited to, thermal activity, thermostability, pH activity, pH stability, substrate/cofactor specificity, improved surface properties, product specificity, increased stability or solubility in the presence of pretreated biomass, improved stability under storage conditions, and chemical stability.

Improved thermostability: The term "improved thermostability" means a variant displaying retention of protease activity after a period of incubation at elevated temperature relative to the parent, either in a buffer or under conditions such as those which exist during product storage/transport or conditions similar to those that exist during industrial use of the variant. Whether or not a variant protease of the invention has an improved thermostability as compared to a parent protease may be determined as described in Example 1. The variant protease of the invention may have an improved thermostability as compared to a parent protease, wherein the improved thermostability is determined as increased relative activity. The variant protease of the invention may have an improved thermostability as compared to a parent protease, wherein the improved thermostability is determined as increased remaining activity.

In one aspect, the thermostability of the variant having protease activity is at least 1.05-fold, e.g., at least 1.1-fold, at least 1.5-fold, at least 1.8-fold, at least 2-fold, at least 5-fold, at least 10-fold, at least 15-fold, at least 20-fold, and at least 25-fold more thermostable than the parent when residual activity is compared using the assay for determining remaining activity (azo-casein) in the Examples.

Modifications, Such as Substitutions, Deletions, Insertions

A protease variant can comprise various types of modifications relative to a template (i.e. a parent or reference protease, or a comparative amino acid sequence such as amino acids 1 to 177 of SEQ ID NO: 2): An amino acid can be substituted with another amino acid; an amino acid can be deleted; an amino acid can be inserted between two residues; as well as any combination of any number of such modifications.

A substitution or extension without any indication of what to substitute or extend with refers to the insertion of any natural, or non-natural, amino acid, except the one that occupies this position in the template.

A substitution means a replacement of an amino acid occupying a position with a different amino acid; a deletion means removal of an amino acid occupying a position; and an insertion means adding 1-3 amino acids adjacent to an amino acid occupying a position. In the present context the term "insertion" is intended to cover also N- and/or C-terminal extensions.

For purposes of the present invention, the mature polypeptide comprised in SEQ ID NO: 2 is used to determine the corresponding amino acid residue in the variant protease. The amino acid sequence of the variant protease is aligned with the mature polypeptide disclosed in SEQ ID NO: 2, and based on the alignment, the amino acid position number corresponding to any amino acid residue in the mature polypeptide disclosed in SEQ ID NO: 2 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later.

Identification of the corresponding amino acid residue in another protease can be confirmed by an alignment of multiple polypeptide sequences using "ClustalW" (Larkin et al., 2007, *Bioinformatics* 23: 2947-2948).

Substitutions.

For an amino acid substitution, the following nomenclature is used: Original amino acid, position, substituted amino acid. Accordingly, the substitution of threonine with alanine at position 226 is designated as "Thr226Ala" or "T226A". Multiple mutations are separated by slash marks ("/"), e.g., "Gly205Arg/Ser411Phe" or "G205R/S411F", representing substitutions at positions 205 and 411 of glycine (G) with arginine (R) and serine (S) with phenylalanine (F), respectively.

Deletions.

For an amino acid deletion, the following nomenclature is used: "Δ", Original amino acid, position. Accordingly, the deletion of glycine at position 195 is designated as "ΔGly195" or "ΔG195". Multiple deletions are separated by slash marks ("/"), e.g., "ΔGly195/ΔSer411" or "ΔG195/ΔS411".

Insertions.

For an amino acid insertion, the following nomenclature is used: Original amino acid, position, original amino acid, inserted amino acid. Accordingly the insertion of lysine after glycine at position 195 is designated "Gly195GlyLys" or "G195GK".

Multiple Alterations.

Variants comprising multiple alterations are separated by slash marks ("/"), e.g., "Arg170Tyr/Gly195Glu" or "R170Y/G195E" representing a substitution of tyrosine and glutamic acid for arginine and glycine at positions 170 and 195, respectively.

Position Numbering

The nomenclature used herein for defining amino acid positions is based on the amino acid sequence of the protease derived from *Thermoascus aurantiacus* CGMCC No. 0670, the mature polypeptide sequence of which is given in the sequence listing as amino acids 1 to 177 of SEQ ID NO: 2 (amino acids 1-177 of SEQ ID NO:2). Accordingly, in the present context, the basis for numbering positions is SEQ ID NO:2 starting with T1 and ending with C177. When used herein the term "mature" part (or sequence) refers to that part of the polypeptide which is secreted by a cell which contains, as part of its genetic equipment, a polynucleotide encoding the polypeptide. In other words, the mature polypeptide part refers to that part of the polypeptide which remains after the signal peptide part, as well as a propeptide part, if any, has been cleaved off. The signal peptide part can be predicted by programs known in the art (e.g. SignalP). Amino acids 1 to 177 of SEQ ID NO: 2 is the expected mature part. Generally, the first amino acid of the mature part of an enzyme can be determined by N-terminal sequencing of the purified enzyme. Any difference between the signal peptide part and the mature part must then be due to the presence of a propeptide.

Methods of Producing a Protease Variant

The present invention relates to methods of producing a protease variant having protease activity and an improved thermostablity when compared to the wild-type parent protease, said method comprising culturing a cell into which has been introduced an expression vector comprising the following operably linked elements:
(a) a transcription promoter,
(b) a polynucleotide molecule encoding a protease variant which has at least 75% identity to the parent protease shown in amino acids 1 to 177 of SEQ ID NO: 2 and which comprises at least one modification as compared to amino acids 1 to 177 of SEQ ID NO: 2 in at least one position selected from the following: 27, 79, 82, 87, 112, 142, 2, 5, 6, 8, 26, 41, 43, 46, 49, 53, 54, 73, 88, 104, 114, 115, 116, 126, 152, 157, 158, and 173,
which polynucleotide molecule is prepared by introducing at least one mutation into a DNA molecule encoding a protease, and
(c) a transcription terminator,
whereby said cell expresses the protease variant encoded by the polynucleotide molecule; and recovering the protease variant.

Preferably the protease applied in the method of the invention exhibiting improved thermostability comprises at least one of the following modifications: A27K, A27G, A27V, Q53K, Q53R, T54R, D79K, D79L, D79M, Y82F, S87G, S87P, A112P, D142L, R2P, AS5, C6R, AG8, N26R, S41R, Y43F, T46R, S49R, A73C, P81R, N88R, D104R, D104P, T114P, S115R, T116V, T124L, T124V, A126V, M152R, S157K, Q158W, and I173V.

In a second aspect, the present invention relates to a protease variant which has at least 75% identity to amino acids 1 to 177 of SEQ ID NO: 2 and which comprises at least one modification as compared to amino acids 1 to 177 of SEQ ID NO: 2 in at least one position selected from the following: 27, 79, 82, 87, 112, 142, 2, 5, 6, 8, 26, 41, 43, 46, 49, 53, 54, 73, 88, 104, 114, 115, 116, 126, 152, 157, 158, and 173. In a more particular embodiment the protease variants comprise at least one modification in at least one position selected from the group consisting of positions: 27, 79, 82, 87, 104, 112, 126, and 142.

Preferably the protease of the invention exhibiting improved thermostability comprises at least one of the following modifications: A27K, A27G, A27V, Q53K, Q53R, T54R, D79K, D79L, D79M, Y82F, S87G, S87P, A112P, D142L, R2P, AS5, C6R, ΔG8, N26R, S41R, Y43F, T46R, S49R, A73C, P81R, N88R, D104P, D104R, T114P, S115R, T116V, T124L, T124V, A126V, M152R, S157K, Q158W, and I173V.

The position numbers refer to the position numbering of amino acids 1 to 177 of SEQ ID NO: 2, as described in the section "Position Numbering." Positions corresponding to these amino acids 1 to 177 of SEQ ID NO: 2 position numbers in other proteases are determined as described above.

The variant protease of the invention is a variant of the protease of amino acids 1 to 177 of SEQ ID NO: 2, viz. it is not identical to amino acids 1 to 177 of SEQ ID NO: 2, as it comprises at least one modification as compared to amino acids 1 to 177 of SEQ ID NO: 2.

In additional preferred embodiments, the protease comprises at least one of the following combinations of modifications:
ΔS5/D79L/S87P,
ΔS5/D79L/S87P/A112P/D142L,
ΔS5/N26R/D79L/S87P/A112P/D142L,
C6R/D79L/S87P,
ΔG8/D79L/S87P,
N26R/D79L/S87P,
N26R/T46R/D79L/S87P/A112P/D142L,
A27G/D79L/S87P/A112P/D142L,
A27K/D79L/S87P/A112P/D142L,
A27K/D79L/S87P/A112P/T124V/D142L,
A27V/D79L/S87P/A112P/D142L,
S41R/D79L/S87P,
S41R/D79L/S87P/A112P/D142L,
S41R/D79L/S87P/A112P/D142L/S157K,
Y43F/D79L/S87P/A112P/D142L,
T46R/D79L/S87P,
T46R/D79L/S87P/A112P/D142L,
T46R/D79L/S87P/T116V/D142L,
S49R/D79L/S87P,
Q53K/D79L/S87P/I173V,
Q53R/D79L/S87P,
T54R/D79L/S87P,
D79L/S87P/A112P,
D79L/P81R/S87P/A112P/D142L,
D79L/S87P,
D79L/S87P/A112P,
D79L/S87P/A112P/D142L,
D79L/S87P/A112P/D142L/S157K,
D79L/S87P/A112P/T124L/D142L,
D79L/S87P/A112P/T124V/A126V/D142L,
D79L/S87P/A112P/T124V/D142L,
D79L/S87P/D104R,
D79L/S87P/D142L,
D79L/S87P/N88R,
D79L/S87P/Q158W,
D79L/S87P/S115R,
D79L/S87P/S157K,
D79L/S87P/T114P,
D79L/S87P/T116V/,
D79L/Y82F/S87P/A112P/T124V/D142L,
D79L/Y82F/S87P/A112P/T124V/D142L,
A27K/D79L/Y82F/S87G/D104P/A112P/A126V/D142L,
A27K/Y82F/S87G/D104P/A112P/A126V/D142L,
A27K/D79L/Y82F/D104P/A112P/A126V/D142L,
A27K/Y82F/D104P/A112P/A126V/D142L.

Strategy for Preparing Variants

A homology model of the structure of SEQ ID NO: 2 was build using PDB entry 1 EB6 as a template. The model was build using the Yasara program (see yasara.org. YASARA Biosciences, Neue-Welt-Hoehe 13/b, 8042 Graz, Austria/Europe).

The model was subjected to molecular dynamics (MD) simulations, electrostatic calculations ancestral sequence reconstruction, consensus sequence calculation, and auto-cleavage site prediction. Based on the modelled structure and the simulation results, modifications were suggested with particular emphasis at improving the thermostability properties.

Based on the structural model, positions close to the active site Zn ion were identified. D142 is an example of a residue close to the active site. Likewise posions exposed to the surface were identified. Positions on the surface interact with the water and are important for stability. Positions 2, 5, 6, 8, 26, 27, 41, 49, 53, 73, 79, 87, 88, 104, 112, 114, 115, 116, 157, 158 are exposed to the surface. The most important of these are 112, 79 and 87.

Molecular dynamics simulations were performed using the GROMACS program version 4 (see gromacs.org. Hess, et al. (2008) J. Chem. Theory Comput. 4: 435-447). Simulations were done at 300K, 400K, 500K in 3 replicates (using different random seeds). Based on the simulations, positions showing high mobility (fluctuations compared to the average structure) or positions showing large displacement (in the average structure compared to the starting model) were selected as candidates for stabilization—either by mutating those directly, or by mutating positions interacting with those. Positions that are highly displaced include positions in the region 144-163, in particular position 152. Positions with high mobility include positions in the regions 5-10, 86-89, and 109-120.

Based on the model, the electrostatic potential in and around the protein was computed and positions with charged amino acids in un-favourable electro static potential (e.g. a negatively charged amino acid in a negative electrostatic potential) and neighbouring positions were marked as targets for mutations. Positions with charged amino acids in unfavorable positions include: 2, 19, 42, 52, 58, 60, 64, 80, 104, 121, 143 and in particular 142 and 79.

Known homologous sequences were simultaneously aligned using the MUSCLE program (Edgar, Robert C. (2004), MUSCLE: multiple sequence alignment with high accuracy and high throughput, Nucleic Acids Research 32(5), 1792-97.). Based on the multiple sequence alignment, several kinds of consensus based analysis were performed. The PAUP program was used to find positions differing from the ancestral gene infered by PAUP. The positions A37, A73, S86, F106, T108, A126, A145, M152, G153, S156, V160, M161, and T165 wherein SEQ ID NO: 2 differs from the consensus based on the alignment were identified. The ancestral reconstruction pointed to positions 73, 86, 126, 152, 153, 156, 38, 50, 94, 109, 135, 136, 142 and in particular to positions 142, 73, 126, 152.

The loss of activity of the protease can be related to autoproteolysis. Based on mass spec analysis of self-digested protein of SEQ ID NO: 2 combined with specificity data from homologous enzymes, a number of positions were suggested: 59, 100, 105, 130, 131, 148 and in particular position 27.

Prolines are known to affect stability, and using the model structure, positions compatible with substituting a proline were identified using the function SUGPRO in the program WHATIF (http://www.cmbi.kun.nl/whatif. WHAT IF Foundation/CMBI, Toernooiveld 1, 6525 ED Nijmegen, The Netherlands).

Cystein bridges can stabilise the structure and by applying the SUGCYS function of the WHATIF program on the model structure positions comparable with cystein substitutions were identified.

The corresponding protease variants were prepared by methods known in the art and tested as described in the experimental part.

Thermostability

Whether or not a variant protease of the invention has an improved thermostability as compared to a parent protease may be determined as described in Example 1. The variant protease of the invention may have an improved thermostability as compared to a parent protease, wherein the improved thermostability is determined as increased relative activity. The variant protease of the invention may have an improved thermostability as compared to a parent protease, wherein the improved thermostability is determined as increased remaining activity.

Thermostability may also be determined using DSC measurements to determine the denaturation temperature, Td, of the purified protease protein. The Td is indicative of the thermostability of the protein: The higher the Td, the higher the thermostability. Accordingly, in a preferred embodiment, the protease of the invention has a Td which is higher than the Td of a reference protease, wherein Td is determined on purified protease samples after buffer-exchange to 20 mM Na-acetate pH 4.5 or 5.5 w/ or w/o 2.5 mM $Zn^{2+}$ by use of a centrifugal filter device (10,000 MWCO) (, using Differential Scanning calorimetry at a 90° C./h scan rate from 20-110° C. (we have a few scans up to 120° C.) in 20 mM Na-acetate buffer. In a preferred embodiment, the Td of the protease of the invention is higher than the Td of the protease of amino acids 1 to 177 of SEQ ID NO: 2, more preferably at least 101% thereof, or at least 102%, 103%, 104%, 105%, 106%, 107%, 108%, 109%, or at least 110% thereof. Even more preferably, the Td of the protease of the invention is at least 120%, 130%, 140%, 150%, 160%, 170%, 180%, or at least 190% of the Td of the protease of amino acids 1 to 177 of SEQ ID NO: 2. In still further particular embodiments, the thermostable protease of the invention has a melting temperature, Tm (or a denaturation temperature, Td), as determined using Differential Scanning calorimetry (DSC) as described in the Examples (i.e. in 20 mM sodium acetate,), of at least 50° C. In still further particular embodiments, the Tm is at least 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or at least 100° C. In particular embodiments, the invention relates to improved thermostability variants of the parent protease of amino acids 1 to 177 of SEQ ID NO: 2 comprising at least one of the following modifications: A27K, A27G, A27V, Q53K, Q53R, T54R, D79K, D79L, D79M, Y82F, S87P, S87G, A112P, D142L, R2P, ΔS5, C6R, ΔG8, N26R, S41R, Y43F, T46R, S49R, A73C, P81R, N88R, D104R, D104P, T114P, S115R, T116V, T124L, T124V, A126V, M152R, S157K, Q158W, and I173V. In a more particular embodiment the modifications are selected from the group consisting of: A27K, D79L, Y82F, S87G, S87P, D104P, A112P, A126V, and D142L.

In particular embodiments, the invention relates to improved thermostability variants of the parent protease of amino acids 1 to 177 of SEQ ID NO: 2 comprising modifications selected from:
ΔS5/D79L/S87P, ΔS5/D79L/S87P/A112P/D142L, ΔS5/ N26R/D79L/S87P/A112P/D142L, C6R/D79L/S87P, ΔG8/ D79L/S87P, N26R/D79L/S87P, N26R/T46R/D79L/S87P/ A112P/D142L, A27G/D79L/S87P/A112P/D142L, A27K/

D79L/S87P/A112P/D142L, A27K/D79L/S87P/A112P/T124V/D142L, A27V/D79L/S87P/A112P/D142L, S41R/D79L/S87P, S41R/D79L/S87P/A112P/D142L, S41R/D79L/S87P/A112P/D142L/S157K, Y43F/D79L/S87P/A112P/D142L, T46R/D79L/S87P, T46R/D79L/S87P/A112P/D142L, T46R/D79L/S87P/T116V/D142L, S49R/D79L/S87P, Q53K/D79L/S87P/I173V, Q53R/D79L/S87P, T54R/D79L/S87P, D79L/S87P/A112P, D79L/P81R/S87P/A112P/D142L, D79L/S87P, D79L/S87P/A112P, D79L/S87P/A112P/D142L, D79L/S87P/A112P/D142L/S157K, D79L/S87P/A112P/T124L/D142L, D79L/S87P/A112P/T124V/A126V/D142L, D79L/S87P/A112P/T124V/D142L, D79L/S87P/D104R, D79L/S87P/D142L, D79L/S87P/N88R, D79L/S87P/Q158W, D79L/S87P/S115R, D79L/S87P/S157K, D79L/S87P/T114P, D79L/S87P/T⁻116V/, D79L/Y82F/S87P/A112P/T⁻124V/D142L, D79L/Y82F/S87P/A112P/T124V/D142L, A27K/D79L/Y82F/S87G/D104P/A112P/A126V/D142L, A27K/Y82F/S87G/D104P/A112P/A126V/D142L, A27K/D79L/Y82F/D104P/A112P/A126V/D142L, A27K/Y82F/D104P/A112P/A126V/D142L.

In one particular embodiment, the invention relates to an improved thermostability variant of the parent protease of amino acids 1 to 177 of SEQ ID NO: 2 comprising the modifications: A27K/D79L/Y82F/S87G/D104P/A112P/A126V/D142L.

In another particular embodiment, the invention relates to an improved thermostability variant of the parent protease of amino acids 1 to 177 of SEQ ID NO: 2 comprising the modifications: A27K/Y82F/S87G/D104P/A112P/A126V/D142L.

In still another particular embodiment, the invention relates to an improved thermostability variant of the parent protease of amino acids 1 to 177 of SEQ ID NO: 2 comprising the modifications: A27K/D79L/Y82F/D104P/A112P/A126V/D142L.

In an even further particular embodiment, the invention relates to an improved thermostability variant of the parent protease of amino acids 1 to 177 of SEQ ID NO: 2 comprising the modifications: A27K/Y82F/D104P/A112P/A126V/D142L.

Nucleic Acid Sequences and Constructs

The present invention also relates to nucleic acid sequences comprising a nucleic acid sequence which encodes a protease variant of the invention.

The term "isolated nucleic acid sequence" refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The nucleic acid sequences of the invention can be prepared by introducing at least one mutation into a template protease coding sequence or a subsequence thereof, wherein the mutant nucleic acid sequence encodes a variant protease.

The introduction of a mutation into the nucleic acid sequence to exchange one nucleotide for another nucleotide may be accomplished by any of the methods known in the art, e.g. by site-directed mutagenesis, by random mutagenesis, or by doped, spiked, or localized random mutagenesis.

Random mutagenesis is suitably performed either as localized or region-specific random mutagenesis in at least three parts of the gene translating to the amino acid sequence shown in question, or within the whole gene. When the mutagenesis is performed by the use of an oligonucleotide, the oligonucleotide may be doped or spiked with the three non-parent nucleotides during the synthesis of the oligonucleotide at the positions which are to be changed. The doping or spiking may be performed so that codons for unwanted amino acids are avoided. The doped or spiked oligonucleotide can be incorporated into the DNA encoding the protease enzyme by any technique, using, e.g., PCR, LCR or any DNA polymerase and ligase as deemed appropriate.

Preferably, the doping is carried out using "constant random doping", in which the percentage of wild-type and mutation in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% mutations in each position. An additional consideration in the choice of a doping scheme is based on genetic as well as protein-structural constraints.

The random mutagenesis may be advantageously localized to a part of the parent protease in question. This may, e.g., be advantageous when certain regions of the enzyme have been identified to be of particular importance for a given property of the enzyme.

Alternative methods for providing variants of the invention include gene shuffling e.g. as described in WO 95/22625 or in WO 96/00343, and the consensus derivation process as described in EP 897985.

Nucleic Acid Constructs

A nucleic acid construct comprises a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

The term "control sequences" is defined herein to include all components, which are necessary or advantageous for the expression of a polynucleotide encoding a polypeptide of the present invention. Each control sequence may be native or foreign to the nucleotide sequence encoding the polypeptide. Such control sequences include, but are not limited to, a leader, polyadenylation sequence, propeptide sequence, transcription promoter, signal peptide sequence, and transcription terminator. At a minimum, the control sequences include a transcription promoter, and transcriptional and translational stop signals. The control sequences may be provided with linkers for the purpose of introducing specific restriction sites facilitating ligation of the control sequences with the coding region of the nucleotide sequence encoding a polypeptide.

The term "operably linked" denotes herein a configuration in which a control sequence is placed at an appropriate position relative to the coding sequence of the polynucleotide sequence such that the control sequence directs the expression of the coding sequence of a polypeptide.

When used herein the term "coding sequence" (CDS) means a nucleotide sequence, which directly specifies the amino acid sequence of its protein product. The boundaries of the coding sequence are generally determined by an open reading frame, which usually begins with the ATG start codon or alternative start codons such as GTG and TTG. The coding sequence may a DNA, cDNA, or recombinant nucleotide sequence Expression Vector The term "expression" includes any step involved in the production of the polypeptide including, but not limited to, transcription, post-transcriptional modification, translation, post-translational modification, and secretion.

The term "expression vector" is defined herein as a linear or circular DNA molecule that comprises a polynucleotide encoding a polypeptide of the invention, and which is operably linked to additional nucleotides that provide for its expression.

A nucleic acid sequence encoding a protease variant of the invention can be expressed using an expression vector which typically includes control sequences encoding a promoter, operator, ribosome binding site, translation initiation signal, and, optionally, a repressor gene or various activator genes.

The recombinant expression vector carrying the DNA sequence encoding a protease variant of the invention may be any vector which may conveniently be subjected to recombinant DNA procedures, and the choice of vector will often depend on the host cell into which it is to be introduced. The vector may be one which, when introduced into a host cell, is integrated into the host cell genome and replicated together with the chromosome(s) into which it has been integrated.

The protease variant may also be co-expressed together with at least one other enzyme of interest, such as a glucoamylase, alpha-amylase, phosphatase, xylanase, galactanase, alpha-galactosidase, protease, phospholipase, and/or beta-glucanase. The enzymes may be co-expressed from different vectors, from one vector, or using a mixture of both techniques. When using different vectors, the vectors may have different selectable markers, and different origins of replication. When using only one vector, the genes can be expressed from one or more promoters. If cloned under the regulation of one promoter (di- or multi-cistronic), the order in which the genes are cloned may affect the expression levels of the proteins. The protease variant may also be expressed as a fusion protein, i.e. that the gene encoding the protease variant has been fused in frame to the gene encoding another protein. This protein may be another enzyme or a functional domain from another enzyme.

Host Cells

The term "host cell", as used herein, includes any cell type which is susceptible to transformation, transfection, transduction, and the like with a nucleic acid construct comprising a polynucleotide of the present invention.

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular microorganisms are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* and *Bacillus thuringiensis*; or a *Streptomyces* cell, e.g., *Streptomyces lividans* and *Streptomyces murinus*, or gram negative bacteria such as *E. coli* and *Pseudomonas* sp. In a preferred aspect, the bacterial host cell is a *Bacillus lentus, Bacillus licheniformis, Bacillus stearothermophilus,* or *Bacillus subtilis* cell. In another preferred aspect, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980).

In an even more preferred aspect, the yeast host cell is a *Candida, Hansenula, Kluyveromyces, Pichia, Saccharomyces, Schizosaccharomyces,* or *Yarrowia* cell.

In a most preferred aspect, the yeast host cell is a *Pichia pastoris, Pichia methanolica, Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Coprinus, Coriolus, Cryptococcus, Filobasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa*, or *Ceriporiopsis subvermispora, Coprinus cinereus, Coriolus hirsutus, Humicola insolens, Humicola lanuginosa, Mucor miehei, Myceliophthora thermophile, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* strain cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proc. Nat. Acad. Sci. USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Vol. 194, pp 182-187, Academic Press, Inc., New York; Ito et al., 1983, *Journal of Bacteriology* 153: 163; and Hinnen et al., 1978, *Proc. Nat. Acad. Sci. USA* 75: 1920.

Methods of Production

The present invention also relates to methods for producing a protease of the present invention comprising (a) cultivating a host cell; and (b) recovering the protease.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, Eds, VCH Publishers, New York, 1989).

Transgenic Plants

The present invention also relates to a transgenic plant, plant part, or plant cell which has been transformed with a nucleotide sequence encoding a polypeptide having protease activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

In a particular embodiment, the polypeptide is targeted to the endosperm storage vacuoles in seeds. This can be obtained by synthesizing it as a precursor with a suitable signal peptide, see Horvath et al in PNAS, Feb. 15, 2000, vol. 97, no. 4, p. 1914-1919.

The transgenic plant can be dicotyledonous (a dicot) or monocotyledonous (a monocot) or engineered variants thereof. Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, triticale (stabilized hybrid of wheat (*Triticum*) and rye (*Secale*), and maize (corn). Examples of dicot plants are tobacco, legumes, such as sunflower (*Helianthus*), cotton (*Gossypium*), lupins, potato, sugar beet, pea, bean and soybean, and cruciferous plants (family Brassicaceae), such as cauliflower, rape seed, and the closely related model organism *Arabidopsis thaliana*. Low-phytate plants as described e.g. in U.S. Pat. No. 5,689,054 and U.S. Pat. No. 6,111,168 are examples of engineered plants.

Examples of plant parts are stem, callus, leaves, root, fruits, seeds, and tubers, as well as the individual tissues comprising these parts, e.g. epidermis, mesophyll, parenchyma, vascular tissues, meristems. Also specific plant cell compartments, such as chloroplast, apoplast, mitochondria, vacuole, peroxisomes, and cytoplasm are considered to be a plant part. Furthermore, any plant cell, whatever the tissue origin, is considered to be a plant part. Likewise, plant parts such as specific tissues and cells isolated to facilitate the utilisation of the invention are also considered plant parts, e.g. embryos, endosperms, aleurone and seed coats.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences are determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific cell compartment, tissue or plant part such as seeds or leaves. Regulatory sequences are, for example, described by Tague et al., 1988, Plant Physiology 86: 506.

For constitutive expression, the following promoters may be used: The 35S-CaMV promoter (Franck et al., 1980, Cell 21: 285-294), the maize ubiquitin 1 (Christensen A H, Sharrock R A and Quail 1992. Maize polyubiquitin genes: structure, thermal perturbation of expression and transcript splicing, and promoter activity following transfer to protoplasts by electroporation), or the rice actin 1 promoter (*Plant Mol. Biol.* 18, 675-689.; Zhang W, McElroy D. and Wu R 1991, Analysis of rice Act1 5' region activity in transgenic rice plants. *Plant Cell* 3, 1155-1165). Organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the *chlorella* virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may be inducible by abiotic treatments such as temperature, drought or modifications in salinity or inducible by exogenously applied substances that activate the promoter, e.g. ethanol, oestrogens, plant hormones like ethylene, abscisic acid, gibberellic acid, and/or heavy metals.

A promoter enhancer element may also be used to achieve higher expression of the polypeptide in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

Still further, the codon usage may be optimized for the plant species in question to improve expression (see Horvath et al referred to above).

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, Science 244: 1293; Potrykus, 1990, Bio/Technology 8: 535; Shimamoto et al., 1989, Nature 338: 274).

Presently, *Agrobacterium*-mediated gene transfer is the method of choice for generating transgenic dicots (for a review, see Hooykas and Schilperoort, 1992, *Plant Molecular Biology* 19: 15-38), and it can also be used for transforming monocots, although other transformation methods are more often used for these plants. Presently, the method of choice for generating transgenic monocots, supplementing the *Agrobacterium* approach, is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated therein the expression construct are selected and regenerated into whole plants according to methods well-known in the art. Often the transformation procedure is designed for the selective elimination of selection genes either during regeneration or in the following generations by using e.g. co-transformation with two separate T-DNA constructs or site specific excision of the selection gene by a specific recombinase.

The present invention also relates to methods for producing a polypeptide of the present invention comprising (a) cultivating a transgenic plant or a plant cell comprising a nucleic acid sequence encoding a polypeptide having protease activity of the present invention under conditions conducive for production of the polypeptide; and (b) recovering the polypeptide.

Compositions and Uses

In still further aspects, the present invention relates to compositions comprising a polypeptide of the present invention, as well as methods of using these.

The polypeptide compositions may be prepared in accordance with methods known in the art and may be in the form of a liquid or a dry composition. For instance, the polypeptide composition may be in the form of granulates or microgranulates. The polypeptide to be included in the composition may be stabilized in accordance with methods known in the art.

The polypeptide and/or composition of the invention may be used for a detergent composition, an animal feed composition, for starch liquefaction, saccharification, and/or fermentation, e.g., as disclosed in WO9220777.

The polypeptide and/or composition of the invention may be used in a process for production of a syrup. For instance, the end product may be glucose, but may also be converted, e.g., by glucose isomerase to fructose or a mixture composed almost equally of glucose and fructose. This mixture, or a mixture further enriched with fructose, is the most commonly used high fructose corn syrup (HFCS) commercialized throughout the world.

The polypeptide and/or composition of the invention may be used in a process for production of a fermentation product. In a particular embodiment the invention relates to a method for producing a fermentation product, comprising (a) fermenting using a fermenting microorganism, and a carbohydrate containing material in the presence of a polypeptide having protease activity of any of:

A) polypeptide having protease activity which has at least 75% identity to the protease shown in amino acids 1 to 177 of SEQ ID NO: 2 and which includes at least one modification as compared to amino acids 1 to 177 of SEQ ID NO: 2 in at least one position selected from the following: 27, 79, 82, 67, 112, 142, 2, 5, 6, 8, 26, 41, 43, 46, 49, 53, 54, 73, 86, 104, 114, 115, 116, 126, 152, 157, 158, and 173, wherein the polypeptide has improved thermostability compared to the protease shown in amino acids 1 to 177 of SEQ ID NO: 2

B) polypeptide of "A" above and having protease activity, which includes at least one modification selected from the following: A27K, A27G, A27V, Q53K, Q53R, T54R, D79K, D79L, D79M, Y82F, S87P, S87G, A112P, P142L, R2P, ΔS5, C6R, ΔG8, N26R, S41R, Y43F, T46R, S49R, A73C, P81R, N88R, D104R, D104P, T114P, S115R, T116V, T124L, T124V, A126V, M152R, S157K, Q158W, and I173V C) polypeptide of "A" above wherein the polypeptide comprises at least one modification in at least one position selected from the group consisting of positions: 27, 79, 82, 87, 104, 112, 126, and 142

D) polypeptide of "C" above wherein the polypeptide comprises at least one of the modifications selected from the group consisting of: A27K, D79L, Y82F, S87G, S87P, D104P, A112P, A126V, and D142L E) polypeptide of A, B or C bating protease activity, which polypeptide comprises a set of modifications seloected from the following: ΔS5/D79L/S97P, ΔS5/D79L/S87P/A112P/D142L, ΔS5/N26R/D79L/S87P/A112P/D142L, C6R/D79L/S87P, ΔG8/D79L/S87P, N26R/D79L/S87P, N26R/T46R/D79L/S87P/A112P/D142L, A27G/D79L/S87P/A112P/D142L, A27K/D79L/S87P/A112P/D142L, A27K/D79L/S87P/A112P/T124V/D142L, A27V/D79L/S87P/A112P/D142L, S41R/D79L/S87P, S41R/D79L/S87P/A112P/D142L, S41R/D79L/S87P/A112P/D142L/S157K, Y43F/D79L/S87P/A112P/D142L, T46R/D79L/S87P, T46R/D79L/S87P/A112P/D142L, T46R/D79L/S87P/T116V/D142L, S49R/D79L/S87P, Q53K/D79L/S87P/I173V, Q53R/D79L/S87P, T54R/D79L/S87P, D79L/ S87P/A112P, D79L/P81R/S87P/A112P/D142L, D79L/S87P, D79L/S87P/A112P, D79L/S87P/A112P/D142L, D79L/S87P/A112P/D142L/S157K, D79L/S87P/A112P/T124L/D142L, D79L/S87P/A112P/T124V/A126V/D142L, D79L/S87P/A112P/T124V/D142L, D79L/S87P/D104R, D79L/S87P/D142L, D79L/S87P/N88R, D79L/S87P/Q158W, D79L/S87P/S115R, D79L/S87P/S157K, D79L/S87P/T114P, D79L/S87P/T116V/, D79L/Y82F/S87P/A112P/T124V/D142L, D79L/Y82F/S87P/A112P/T124V/D142L A27K/D79L/Y82F/S87G/D104P/A112P/A126V/D142L, A27K/Y82F/S87G/D104P/A112P/A126V/D142L, A27K/D79L/Y82F/D104P/A112P/A126V/D142L, A27K/Y82F/D104P/A112P/A126V/D142L, and (b) producing the fermentation product from the fermented carbohydrate containing material.

Fermentation products include alcohols (e.g., ethanol, methanol, butanol, 1,3-propanediol); organic acids (e.g., citric acid, acetic acid, itaconic acid, lactic acid, gluconic acid, gluconate, lactic acid, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, $B_{12}$, beta-carotene); hormones, and other compounds which are difficult to produce synthetically. Fermentation processes are also commonly used to produce consumable alcohol (e.g., beer and wine). A preferred fermentation product is ethanol, e.g., industrial ethanol, fuel ethanol and/or potable ethanol. Other preferred fermentation products include the co-products from the ethanol fermentation process, e.g., distillers dried grain (DDG).

In a preferred embodiment starch is liquefied in the presence of an alpha-amylase, the liquefied mash is saccharified in the presence of a glucoamylase. The saccharified mash is fermented with a yeast; and (d) the ethanol produced is recovered. In the process, a polypeptide of the invention is added to the mash prior to/during liquefaction, or saccharification and/or to the hydrolysed starch and sugars during the fermentation.

Preferably the compositions comprising a polypeptide of the present invention comprises at least one other polypeptide selected from amongst amylase such as, for example, alpha-amylase (EC 3.2.1.1), glucoamylase (EC 3.2.1.3) and pullulanase (EC 3.2.1.41); phytase (EC 3.1.3.8 or 3.1.3.26); phosphatase (EC 3.1.3.1; EC 3.1.3.2; EC 3.1.3.39); xylanase (EC 3.2.1.8); galactanase (EC 3.2.1.89); alpha-galactosidase (EC 3.2.1.22); protease (EC 3.4.-.-), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); and/or beta-glucanase (EC 3.2.1.4 or EC 3.2.1.6).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

EXAMPLES

Chemicals used were commercial products of at least reagent grade.

Example 1

Preparation of Variants, and Test of Thermostability

Strains and Plasmids

*E. coli* DH12S (available from Gibco BRL) was used for yeast plasmid rescue. pJTP000 is a *S. cerevisiae* and *E. coli* shuttle vector under the control of TPI promoter, constructed from pJC039 described in WO 01/92502, in which the *Thermoascus aurantiacus* M35 protease gene (WO 03048353) has been inserted.

*Saccharomyces cerevisiae* YNG318 competent cells: MATa Dpep4[cir+] ura3-52, leu2-D2, h is 4-539 was used for protease variants expression. It is described in J. Biol. Chem. 272 (15), pp 9720-9727, 1997.

Media and Substrates

10× Basal solution: Yeast nitrogen base w/o amino acids (DIFCO) 66.8 g/l, succinate 100 g/l, NaOH 60 g/l.

SC-glucose: 20% glucose (i.e., a final concentration of 2%=2 g/100 ml)) 100 ml/l, 5% threonine 4 ml/l, 1% tryptophan10 ml/l, 20% casamino acids 25 ml/l, 10× basal solution 100 ml/l. The solution is sterilized using a filter of a pore size of 0.20 micrometer. Agar (2%) and $H_2O$ (approx. 761 ml) is autoclaved together, and the separately sterilized SC-glucose solution is added to the agar solution.

YPD: Bacto peptone 20 g/l, yeast extract 10 g/l, 20% glucose 100 ml/l.

YPD+Zn: YPD+0.25 mM $ZnSO_4$.

PEG/LiAc solution: 40% PEG4000 50 ml, 5 M Lithium Acetate 1 ml.

96 well Zein micro titre plate:

Each well contains 200 microL of 0.05-0.1% of zein (Sigma), 0.25 mM $ZnSO_4$ and 1% of agar in 20 mM sodium acetate buffer, pH 4.5.

DNA Manipulations

Unless otherwise stated, DNA manipulations and transformations were performed using standard methods of molecular biology as described in Sambrook et al. (1989) Molecular cloning: A laboratory manual, Cold Spring Harbor lab. Cold Spring Harbor, N.Y.; Ausubel, F. M. et al. (eds.) "*Current protocols in Molecular Biology*", John Wiley and Sons, 1995; Harwood, C. R. and Cutting, S. M. (Eds.).

Yeast Transformation

Yeast transformation was performed using the lithium acetate method. 0.5 microL of vector (digested by restriction endnucleases) and 1 microL of PCR fragments is mixed. The DNA mixture, 100 microL of YNG318 competent cells, and 10 microL of YEAST MAKER carrier DNA (Clontech) is added to a 12 ml polypropylene tube (Falcon 2059). Add 0.6 ml PEG/LiAc solution and mix gently. Incubate for 30 min at 30° C., and 200 rpm followed by 30 min at 42° C. (heat shock). Transfer to an eppendorf tube and centrifuge for 5 sec. Remove the supernatant and resolve in 3 ml of YPD. Incubate the cell suspension for 45 min at 200 rpm at 30° C. Pour the suspension to SC-glucose plates and incubate 30° C. for 3 days to grow colonies. Yeast total DNA are extracted by Zymoprep Yeast Plasmid Miniprep Kit (ZYMO research).

DNA Sequencing

*E. coli* transformation for DNA sequencing was carried out by electroporation (BIO-RAD Gene Pulser). DNA Plasmids were prepared by alkaline method (Molecular Cloning, Cold Spring Harbor) or with the Qiagen® Plasmid Kit. DNA fragments were recovered from agarose gel by the Qiagen gel extraction Kit. PCR was performed using a PTC-200 DNA Engine. The ABI PRISM™ 310 Genetic Analyzer was used for determination of all DNA sequences.

Construction of Protease Expression Vector

The Themoascus M35 protease gene was amplified with the primer pair Prot F (SEQ ID NO: 3) and Prot R (SEQ ID NO: 4). The resulting PCR fragments were introduced into *S. cerevisiae* YNG318 together with the pJC039 vector (described in WO2001/92502) digested with restriction enzymes to remove the *Humicola insolens* cutinase gene.

The Plasmid in yeast clones on SC-glucose plates was recovered to confirm the internal sequence and termed as pJTP001.

Construction of Yeast Library and Site-Directed Variants

Library in yeast and site-directed variants were constructed by SOE PCR method (Splicing by Overlap Extension, see "PCR: A practical approach", p. 207-209, Oxford University press, eds. McPherson, Quirke, Taylor), followed by yeast in vivo recombination.

General Primers for Amplification and Sequencing

The primers AM34 (SEQ ID NO:5) and AM35 (SEQ ID NO:6) were used to make DNA fragments containing any mutated fragments by the SOE method together with degenerated primers (AM34+Reverse primer and AM35+forward primer) or just to amplify a whole protease gene (AM34+AM35).

| PCR reaction system: | Conditions: | |
|---|---|---|
| 48.5 microL $H_2O$ | 1 | 94° C. 2 min |
| 2 beads puRe Taq Ready-To-Go PCR (Amersham Biosciences) | 2 | 94° C. 30 sec |
| 0.5 micro L × 2 100 pmole/microL of primers | 3 | 55° C. 30 sec |
| 0.5 microL template DNA | 4 | 72° C. 90 sec |
| | 2-4 | 25 cycles |
| | 5 | 72° C. 10 min |

DNA fragments were recovered from agarose gel by the Qiagen gel extraction Kit. The resulting purified fragments were mixed with the vector digest. The mixed solution was introduced into *Saccharomyces cerevisiae* to construct libraries or site-directed variants by in vivo recombination.

Relative Activity Assay

Yeast clones on SC-glucose were inoculated to a well of a 96-well micro titre plate containing YPD+Zn medium and cultivated at 28° C. for 3 days. The culture supernatants were applied to a 96-well zein micro titer plate and incubated at least 2 temperatures (ex. 60° C. and 65° C., 70° C. and 75° C., 70° C. and 80° C.) for more than 4 hours or overnight. The turbidity of zein in the plate was measured as A630 and the relative activity (higher/lower temperatures) was determined as an indicator of thermoactivity improvement. The clones with higher relative activity than the parental variant were selected and the sequence was determined.

Remaining Activity Assay

Yeast clones on SC-glucose were inoculated to a well of a 96-well micro titre plate and cultivated at 28° C. for 3 days. Protease activity was measured at 65° C. using azo-casein (Megazyme) after incubating the culture supernatant in 20 mM sodium acetate buffer, pH 4.5, for 10 min at a certain temperature (80° C. or 84° C. with 4° C. as a reference) to determine the remaining activity. The clones with higher remaining activity than the parental variant were selected and the sequence was determined.

Azo-Casein Assay 20 microL of samples were mixed with 150 microL of substrate solution (4 ml of 12.5% azo-casein in ethanol in 96 ml of 20 mM sodium acetate, pH 4.5, containing 0.01% triton-100 and 0.25 mM $ZnSO_4$) and incubated for 4 hours or longer.

After adding 20 microL/well of 100% trichloroacetic acid (TCA) solution, the plate was centrifuge and 100 microL of supernatants were pipette out to measure A440.

Expression of Protease Variants in *Aspergillus oryzae*

The constructs comprising the protease variant genes were used to construct expression vectors for *Aspergillus*. The *Aspergillus* expression vectors consist of an expression cassette based on the *Aspergillus niger* neutral amylase II promoter fused to the *Aspergillus nidulans* triose phosphate isomerase non translated leader sequence (Pna2/tpi) and the *Aspergillus niger* amyloglycosidase terminator (Tamg). Also present on the plasmid was the *Aspergillus* selective marker amdS from *Aspergillus nidulans* enabling growth on acetamide as sole nitrogen source.

The expression plasmids for protease variants were transformed into *Aspergillus* as described in Lassen et al. (2001), *Appl. Environ. Microbiol.* 67, 4701-4707. For each of the constructs 10-20 strains were isolated, purified and cultivated in shake flasks.

Purification of Expressed Variants
1. Adjust pH of the 0.22 μm filtered fermentation sample to 4.0.
2. Put the sample on an ice bath with magnetic stirring. Add (NH4)2SO4 in small aliquots (corresponding to approx. 2.0-2.2 M (NH4)2SO4 not taking the volume increase into account when adding the compound).
3. After the final addition of (NH4)2SO4, incubate the sample on the ice bath with gentle magnetic stirring for min. 45 min.
4. Centrifugation: Hitachi himac CR20G High-Speed Refrigerated Centrifuge equipped with R20A2 rotor head, 5° C., 20,000 rpm, 30 min.
5. Dissolve the formed precipitate in 200 ml 50 mM Na-acetate pH 4.0.
6. Filter the sample by vacuum suction using a 0.22 μm PES PLUS membrane (IWAKI).
7. Desalt/buffer-exchange the sample to 50 mM Na-acetate pH 4.0 using ultrafiltration (Vivacell 250 from Vivascience equipped with 5 kDa MWCO PES membrane) overnight in a cold room. Dilute the retentate sample to 200 ml using 50 mM Na-acetate pH 4.0. The conductivity of sample is preferably less than 5 mS/cm.
8. Load the sample onto a cation-exchange column equilibrated with 50 mM Na-acetate pH 4.0. Wash unbound sample out of the column using 3 column volumes of binding buffer (50 mM Na-acetate pH 4.0), and elute the sample using a linear gradient, 0-100% elution buffer (50 mM Na-acetate+1 M NaCl pH 4.0) in 10 column volumes.
9. The collected fractions are assayed by an endo-protease assay (cf. below) followed by standard SDS-PAGE (reducing conditions) on selected fractions. Fractions are pooled based on the endo-protease assay and SDS-PAGE.

Endo-Protease Assay
1. Protazyme OL tablet/5 ml 250 mM Na-acetate pH 5.0 is dissolved by magnetic stirring (substrate: endo-protease Protazyme AK tablet from Megazyme—cat. #PRAK 11/08).
2. With stirring, 250 microL of substrate solution is transferred to a 1.5 ml Eppendorf tube.
3. 25 microL of sample is added to each tube (blank is sample buffer).
4. The tubes are incubated on a Thermomixer with shaking (1000 rpm) at 50° C. for 15 minutes.
5. 250 microL of 1 M NaOH is added to each tube, followed by vortexing.
6. Centrifugation for 3 min. at 16,100×G and 25° C.
7. 200 microL of the supernatant is transferred to a MTP, and the absorbance at 590 nm is recorded.

Results

TABLE 1

Relative activity of protease variants. Numbering of substitution(s) starts from N-terminal of the mature peptide in amino acids 1 to 177 of SEQ ID NO: 2.

| Variant | Substitution(s) | Relative activity 65° C./60° C. |
|---|---|---|
| WT | none | 31% |
| JTP004 | S87P | 45% |
| JTP005 | A112P | 43% |
| JTP008 | R2P | 71% |
| JTP009 | D79K | 69% |
| JTP010 | D79L | 75% |
| JTP011 | D79M | 73% |
| JTP012 | D79L/S87P | 86% |
| JTP013 | D79L/S87P/A112P | 90% |
| JTP014 | D79L/S87P/A112P | 88% |
| JTP016 | A73C | 52% |
| JTP019 | A126V | 69% |
| JTP021 | M152R | 59% |

TABLE 2

Relative activity of protease variants. Numbering of substitution(s) starts from N-terminal of the mature peptide in amino acids 1 to 177 of SEQ ID NO: 2.

| Variant | Substitution(s) and/or deletion (S) | 70° C./65° C. | 75° C./65° C. | 75° C./70° C. |
|---|---|---|---|---|
| WT | none | 59% | 17% | |
| JTP036 | D79L/S87P/D142L | 73% | 73% | |
| JTP040 | T54R/D79L/S87P | | 71% | |
| JTP042 | Q53K/D79L/S87P/I173V | | 108% | |
| JTP043 | Q53R/D79L/S87P | | 80% | |
| JTP045 | S41R/D79L/S87P | | 82% | |
| JTP046 | D79L/S87P/Q158W | | 96% | |
| JTP047 | D79L/S87P/S157K | | 85% | |
| JTP048 | D79L/S87P/D104R | | 88% | |
| JTP050 | D79L/S87P/A112P/D142L | | 88% | |
| JTP051 | S41R/D79L/S87P/A112P/D142L | | | 102% |
| JTP052 | D79L/S87P/A112P/D142L/S157K | | | 111% |
| JTP053 | S41R/D79L/S87P/A112P/D142L/S157K | | | 113% |
| JTP054 | ΔS5/D79L/S87P | | | 92% |
| JTP055 | ΔG8/D79L/S87P | | | 95% |
| JTP059 | C6R/D79L/S87P | | | 92% |
| JTP061 | T46R/D79L/S87P | | | 111% |
| JTP063 | S49R/D79L/S87P | | | 94% |
| JTP064 | D79L/S87P/N88R | | | 92% |
| JTP068 | D79L/S87P/T114P | | | 99% |
| JTP069 | D79L/S87P/S115R | | | 103% |
| JTP071 | D79L/S87P/T116V | | | 105% |
| JTP072 | N26R/D79L/S87P | | 92% | |
| JTP077 | A27K/D79L/S87P/A112P/D142L | | 106% | |
| JTP078 | A27V/D79L/S87P/A112P/D142L | | 100% | |
| JTP079 | A27G/D79L/S87P/A112P/D142L | | 104% | |

TABLE 3

Relative activity of protease variants. Numbering of substitution(s) starts from N-terminal of the mature peptide in amino acids 1 to 177 of SEQ ID NO: 2.

| Variant | Substitution(s) and/or deletion(s) | Relative activity 75° C./ 65° C. | Remaining activity 80° C. | Remaining activity 84° C. |
|---|---|---|---|---|
| JTP082 | ΔS5/D79L/S87P/A112P/D142L | 129% | | 53% |
| JTP083 | T46R/D79L/S87P/A112P/D142L | 126% | | |
| JTP088 | Y43F/D79L/S87P/A112P/D142L | 119% | | |
| JTP090 | D79L/S87P/A112P/T124L/D142L | 141% | | |
| JTP091 | D79L/S87P/A112P/T124V/D142L | 154% | 43% | |
| JTP092 | ΔS5/N26R/D79L/S87P/A112P/D142L | | | 60% |
| JTP095 | N26R/T46R/D79L/S87P/A112P/D142L | | | 62% |
| JTP096 | T46R/D79L/S87P/T116V/D142L | | | 67% |
| JTP099 | D79L/P81R/S87P/A112P/D142L | | | 80% |
| JTP101 | A27K/D79L/S87P/A112P/T124V/D142L | | 81% | |
| JTP116 | D79L/Y82F/S87P/A112P/T124V/D142L | | 59% | |
| JTP117 | D79L/Y82F/S87P/A112P/T124V/D142L | | 94% | |
| JTP127 | D79L/S87P/A112P/T124V/A126V/D142L | | 53% | |

TABLE 4

Relative activity of protease variants. Numbering of substitution(s) starts from N-terminal of the mature peptide in amino acids 1 to 177 of SEQ ID NO: 2.

| Variant | Substitutions | Relative activity 75° C./70° C. | Relative activity 80° C./70° C. | Relative activity 85° C./70° C. |
|---|---|---|---|---|
| JTP050 | D79L S87P A112P D142L | 55% | 23% | 9% |
| JTP134 | D79L Y82F S87P A112P D142L | | 40% | |
| JTP135 | S38T D79L S87P A112P A126V D142L | | 62% | |
| JTP136 | D79L Y82F S87P A112P A126V D142L | | 59% | |
| JTP137 | A27K D79L S87P A112P A126V D142L | | 54% | |
| JTP140 | D79L S87P N98C A112P G135C D142L | 81% | | |
| JTP141 | D79L S87P A112P D142L T141C M161C | 68% | | |
| JTP143 | S36P D79L S87P A112P D142L | 69% | | |
| JTP144 | A37P D79L S87P A112P D142L | 57% | | |
| JTP145 | S49P D79L S87P A112P D142L | 82% | 59% | |
| JTP146 | S50P D79L S87P A112P D142L | 83% | 63% | |
| JTP148 | D79L S87P D104P A112P D142L | 76% | 64% | |
| JTP161 | D79L Y82F S87G A112P D142L | | 30% | 12% |
| JTP180 | S70V D79L Y82F S87G Y97W A112P D142L | | 52% | |
| JTP181 | D79L Y82F S87G Y97W D104P A112P D142L | | 45% | |
| JTP187 | S70V D79L Y82F S87G A112P D142L | | 45% | |
| JTP188 | D79L Y82F S87G D104P A112P D142L | | 43% | |
| JTP189 | D79L Y82F S87G A112P A126V D142L | | 46% | |
| JTP193 | Y82F S87G S70V D79L D104P A112P D142L | | | 15% |
| JTP194 | Y82F S87G D79L D104P A112P A126V D142L | | | 22% |
| JTP196 | A27K D79L Y82F S87G D104P A112P A126V D142L | | | 18% |

TABLE 5

Relative activity of protease variants. Numbering of substitution(s) starts from N-terminal of the mature peptide in amino acids 1 to 177 of SEQ ID NO: 2.

| Variant | Substitutions | Relative activity 75° C./70° C. | Relative activity 80° C./70° C. |
|---|---|---|---|
| JTP196 | A27K D79L Y82F S87G D104P A112P A126V D142L | 102% | 55% |
| JTP210 | A27K Y82F S87G D104P A112P A126V D142L | 107% | 36% |
| JTP211 | A27K D79L Y82F D104P A112P A126V D142L | 94% | 44% |
| JTP213 | A27K Y82F D104P A112P A126V D142L | 103% | 37% |

Example 2

Temperature Profile of Selected Variants Using Purified Enzymes

Selected variants showing good thermo-stability were purified and the purified enzymes were used in a zein-BCA assay as described below. The remaining protease activity was determined at 60° C. after incubation of the enzyme at elevated temperatures as indicated for 60 min.

Zein-BCA assay:

Zein-BCA assay was performed to detect soluble protein quantification released from zein by variant proteases at various temperatures.

Protocol:

1) Mix 10 ul of 10 ug/ml enzyme solutions and 100 ul of 0.025% zein solution in a micro titer plate (MTP).

2) Incubate at various temperatures for 60 min.

3) Add 10 ul of 100% trichloroacetic acid (TCA) solution.

4) Centrifuge MTP at 3500 rpm for 5 min.

5) Take out 15 ul to a new MTP containing 100 ul of BCA assay solution (Pierce Cat#:23225, BCA Protein Assay Kit).

6) Incubate for 30 min. at 60° C.

7) Measure A562.

The results are shown in Table 6. All of the tested variants showed an improved thermo-stability as compared to the wt protease.

TABLE 6

Zein-BCA assay

Sample incubated 60 min at indicated temperatures (° C.)
(μg/ml Bovine serum albumin equivalent peptide released)

| WT/Variant | 60° C. | 70° C. | 75° C. | 80° C. | 85° C. | 90° C. | 95° C. |
|---|---|---|---|---|---|---|---|
| WT | 94 | 103 | 107 | 93 | 58 | 38 | |
| JTP050 | 86 | 101 | 107 | 107 | 104 | 63 | 36 |
| JTP077 | 82 | 94 | 104 | 105 | 99 | 56 | 31 |
| JTP188 | 71 | 83 | 86 | 93 | 100 | 75 | 53 |
| JTP196 | 87 | 99 | 103 | 106 | 117 | 90 | 38 |

---

The invention claimed is:

1. An isolated polypeptide comprising an amino acid sequence having at least 95% sequence identity to residues 1-177 of SEQ ID NO: 2 and a substitution at position 142 of SEQ ID NO: 2, wherein the amino acid sequence has the protease specificity of the amino acid sequence of 1-177 of SEQ ID NO: 2 and has, at 80° C.-95° C., improved thermostability compared to the amino acids sequence of SEQ ID NO: 1-177 of SEQ ID NO: 2.

2. The isolated polypeptide of claim 1, wherein the substitution at position 142 is D142L.

3. The isolated polypeptide of claim 1, wherein the amino acid sequence has at least 99% identity to residues 1-177 of SEQ ID NO: 2.

4. The isolated polypeptide of claim 3, wherein the substitution at position 142 is D142L.

* * * * *